United States Patent
Kagias et al.

(10) Patent No.: US 10,514,342 B2
(45) Date of Patent: Dec. 24, 2019

(54) OMNIDIRECTIONAL SCATTERING- AND BIDIRECTIONAL PHASE-SENSITIVITY WITH SINGLE SHOT GRATING INTERFEROMETRY

(71) Applicant: PAUL SCHERRER INSTITUT, Villigen Psi (CH)

(72) Inventors: Matias Kagias, Zurich (CH); Marco Stampanoni, Endingen (CH); Zhentian Wang, Brugg (CH)

(73) Assignee: Paul Scherrer Institut, Villigen PSI (CH)

( * ) Notice: Subject to any disclaimer, the term of this patent is extended or adjusted under 35 U.S.C. 154(b) by 98 days.

(21) Appl. No.: 15/755,215

(22) PCT Filed: Jul. 20, 2016

(86) PCT No.: PCT/EP2016/067234
§ 371 (c)(1),
(2) Date: Feb. 26, 2018

(87) PCT Pub. No.: WO2017/032512
PCT Pub. Date: Mar. 2, 2017

(65) Prior Publication Data
US 2018/0246046 A1 Aug. 30, 2018

(30) Foreign Application Priority Data
Aug. 25, 2015 (EP) .................... 15182383

(51) Int. Cl.
*G01N 23/041* (2018.01)
*A61B 6/00* (2006.01)
(Continued)

(52) U.S. Cl.
CPC .......... *G01N 23/041* (2018.02); *A61B 6/032* (2013.01); *A61B 6/4035* (2013.01);
(Continued)

(58) Field of Classification Search
None
See application file for complete search history.

(56) References Cited

U.S. PATENT DOCUMENTS

2015/0071402 A1 3/2015 Handa
2015/0243397 A1* 8/2015 Yun .................. G01N 23/20075
378/36
(Continued)

FOREIGN PATENT DOCUMENTS

CN 104833685 A 8/2015
EP 2652708 A1 10/2013
(Continued)

*Primary Examiner* — Hoon K Song
(74) *Attorney, Agent, or Firm* — Laurence Greenberg; Werner Stemer; Ralph Locher

(57) ABSTRACT

X-ray scattering imaging can provide complementary information about the unresolved microstructures of a sample. The scattering signal can be accessed with various methods based on coherent illumination, which span from self-imaging to speckle scanning. The directional sensitivity of the existing methods is limited to a few directions on the imaging plane and it requires the scanning of the optical components, or the rotation of either the sample or the imaging setup, if the full range of possible scattering directions is desired. A new arrangement is provided that allows the simultaneous acquisition of the scattering images in all possible directions in a single shot. This is achieved by a specialized phase grating and a device for recording the generated interference fringe with sufficient spatial resolution. The technique decouples the sample dark-field signal with the sample orientation, which can be crucial for medical and industrial applications.

15 Claims, 3 Drawing Sheets

(51) Int. Cl.
  *G01N 23/20* (2018.01)
  *G01N 23/201* (2018.01)
  *G01N 23/04* (2018.01)
  *A61B 6/03* (2006.01)
  *G02B 5/18* (2006.01)
  *G21K 1/06* (2006.01)
(52) U.S. Cl.
  CPC .......... *A61B 6/4092* (2013.01); *A61B 6/4233* (2013.01); *A61B 6/4291* (2013.01); *A61B 6/484* (2013.01); *G01N 23/04* (2013.01); *G01N 23/201* (2013.01); *G01N 23/20075* (2013.01); *G02B 5/1838* (2013.01); *G02B 5/1871* (2013.01); *G21K 1/06* (2013.01); *G21K 2207/005* (2013.01)

(56) References Cited

U.S. PATENT DOCUMENTS

| 2015/0247811 A1* | 9/2015 | Yun | G01N 23/223 378/45 |
| 2015/0260663 A1* | 9/2015 | Yun | G01N 23/20075 378/36 |

FOREIGN PATENT DOCUMENTS

| WO | 2011011014 A1 | 1/2011 |
| WO | 2012080125 A1 | 6/2012 |

\* cited by examiner

OMNIDIRECTIONAL SCATTERING- AND BIDIRECTIONAL PHASE-SENSITIVITY WITH SINGLE SHOT GRATING INTERFEROMETRY

BACKGROUND OF THE INVENTION

Field of the Invention

The present invention relates to an arrangement for x-rays, in particular hard x-rays, for obtaining quantitative x-ray images from a sample.

X-ray grating interferometry (GI) can provide simultaneously three complimentary contrasts: absorption, differential phase and small-angle scattering. Each contrast corresponds to a different physical interaction of the incoming x-rays with the sample under examination. The phase signal is highly sensitive to the electron density variations in the sample and can reveal differences between materials with similar absorption properties. The scattering signal is able to access unresolved structure variations of the sample in (sub) micrometer scale, which is beyond the resolution capability of the imaging modality. It has been demonstrated that both differential phase and scattering signals can provide valuable information additional to the traditional absorption contrast in medical imaging, material science and non-destructive testing. Especially, the scattering signal has drawn great attention due to its success in providing quantitative or inaccessible structural information in radiographic applications.

In general, the scattering signal exhibits highly directional behavior if the underlying sample contains ordered internal structure. However, up to now imaging with grating interferometers has been mainly performed with linear gratings and the scattering sensitivity is only perpendicular to the grating lines, for instance, one implementation is descripted in Ref. [1] using linear gratings. Therefore, in order to obtain multiple-direction scattering (or differential phase) sensitivity, either the sample or the interferometer needs to be rotated, which is a time-consuming procedure. The usage of 2D gratings can mitigate the issue and provide up to four directions scattering sensitivity, however this approach requires a complicated imaging setup since one of the gratings needs to be scanned in a raster manner. Moreover, the noise performance is not the same in all directions due to different modulation orders of the phase stepping curves. An alternative speckle scanning technique is proposed to sense the scattering signal by scanning a membrane in the direction of interest, but this approach has similar shortcomings as the linear grating interferometric designs since the scattering sensitivity only corresponds to the scan direction.

To cope with samples containing unknown directional structures, it would be favorable to design an imaging system with the following characteristics:

Omnidirectional scattering sensitivity

Differential phase contrast in two directions to allow integration of the phase signal Fast acquisition Straightforward mechanical setup: no need for scanning/rotation of sample or optical elements.

Such a system would assure that all micro-structures, highly ordered or not, can be detected with the same sensitivity without taking any demanding precautions of the alignment of the sample with the optical axis.

SUMMARY OF THE INVENTION

These objectives are achieved according to the present invention by a single-shot imaging arrangement according to the main claim and preferred embodiments according to the dependent claims.

The invention discloses an arrangement for x-rays, in particular hard x-rays, for obtaining quantitative x-ray images from a sample, comprising:
a) an X-ray source, preferably a standard polychromatic X-ray source (1);
b) one phase-shift periodic structure G1 (4);
c) a position-sensitive detector (PSD) (5) with spatially modulated detection sensitivity having a number of individual pixels;
d) means for recording the images of the detector;
e) means for evaluating the intensities in a single shot image in order to obtain the characteristics of the sample including absorption, differential phase contrast and directional (small-angle) scattering contrast, preferably for specified regions of pixels; and
f) an optional absorption grating or a mask (G0) in front of, or embedded into the X-ray source (2);
wherein the phase-shift periodic structure G1 is:
i) a 2D periodic structure composed of unit cells, said unit cells are circular gratings; the period of the unit cells is P and that of the circular gratings is p, wherein the periodic structures in the circular grating generate a considerable X-ray phase shift difference, which is preferably of $\pi/2$ or odd multiples thereof, hereinafter referred to as $\pi/2$ shift; or $\pi$ or $\pi+N\times 2\times\pi$, hereinafter referred to as $\pi$ shift, where N is an integer number; or
ii) a honeycomb structure composed of unit cells, each unit cell is a circular grating which allows the highest filling factor of circular structures on a 2D plane such periodic structure; the periodic structures in the circular grating generate a considerable X-ray phase shift difference, which is preferably of $\pi/2$ or odd multiples thereof, hereinafter referred to as $\pi/2$ shift; or $\pi$ or $\pi+N\times 2\times\pi$, hereinafter referred to as $\pi$ shift, where N is an integer number.

This single-shot imaging arrangement is capable of omnidirectional scattering sensitivity, acquisition of differential phase contrast signals in vertical and horizontal directions and absorption contrast without the rotation or shift of optical elements or the sample under examination.

Preferably, the phase-shift periodic structure G1 is made by deep etching into silicon, a polymer or similar material, preferable for low energy X-ray photons; or deposit heavy metal into gaps of low-absorbing structure or grow heavy metal on low-absorbing substrate, in either case the metal is used as the phase shift material, preferably for high energy X-ray photons.

A further preferred embodiment of the present invention is achieved, when the phase-shift periodic structure G1 creates a periodic interference pattern with a repetition of each unit cell P' and the period within each unit cell is p' at a known distance (Talbot effect) downstream on the PSD; P' and p' match the radius of curvature of an incident wavefront by relation $$p' = \frac{1}{\eta} p \frac{d_1 + l_1}{l_1}, \quad P' = \frac{1}{\eta} P \frac{d_1 + l_1}{l_1}$$

where $l_1$ is the distance between the X-ray source (or the absorption grating or mask G0 if G0 is used) to the phase-shift periodic structure (G1), $d_1$ is the distance between the phase-shift periodic structure (G1) and the created self-image $\eta=1$ for $\pi/2$ shift grating while $\eta=2$ for $\pi$ shift grating.

Typically, the detector can be a charge integrating detector with single photon sensitivity which has enhanced the spatial resolution using charge sharing effect.

For the absorption grating or mask G0 an advantageous design can be achieved when the absorption grating or mask G0 is a 2D chessboard/mesh-type grating with pitch of $$p_0 = p \times \frac{l_1}{d_1}$$

or integer multiples thereof, or when G0 is not used but the X-ray source comprises 2D array of individual sources that may be mutually incoherent and whose lateral separation $$p_0 = p \times \frac{l_1}{d_1}$$

or integer multiples thereof.

Further, in order to provide a simple arrangement for the sample handling, a mechanism can be comprised to place the sample to be investigated between the X-ray source (or G0 if G0 is used) and the phase-shift periodic structure G1, or between the phase-shift periodic structure G1 and the detector.

Suitable analysis means may provide for an analysis procedure being implemented for obtaining the absorption, differential phase contrast and directional scattering contrasts of the sample that comprises the steps of recording two intensity images of the interference pattern (with sample and without sample) on the detector.

Further, the analysis means may comprise means to detect the location of individual unit cells on the recorded flat image by using the circular nature of the phase-shift periodic structure G1, that being said, an intensity maximum is observed in the center of a unit cell.

Furthermore, the analysis means may comprise means to calculate the shift between the flat and sample images of each unit cell, preferably achieved either with Fourier based methods and/or Hilbert transform methods by calculating the analytical signal or spatial correlation methods.

Further, the analysis means may comprise means to evaluate the radial visibility reduction for every angle in order to obtain omnidirectional scattering images, preferably accomplished by Fourier methods from the following formula $$C(n, m, \theta) = \frac{R_k^s R_0^f}{R_k^f R_0^f}.$$

Preferably, the mechanism to handle the sample may also comprise means for rotating the sample relatively to the remaining components to perform data collection for a tomographic scan.

Advantageously, the phase-shift periodic structure G1 may be an absorption grating.

BRIEF DESCRIPTION OF THE SEVERAL VIEWS OF THE DRAWING

Preferred embodiments of the present invention are hereinafter described in more detail with reference to the attached drawings which depict in.

DESCRIPTION OF THE INVENTION

Figure 1:
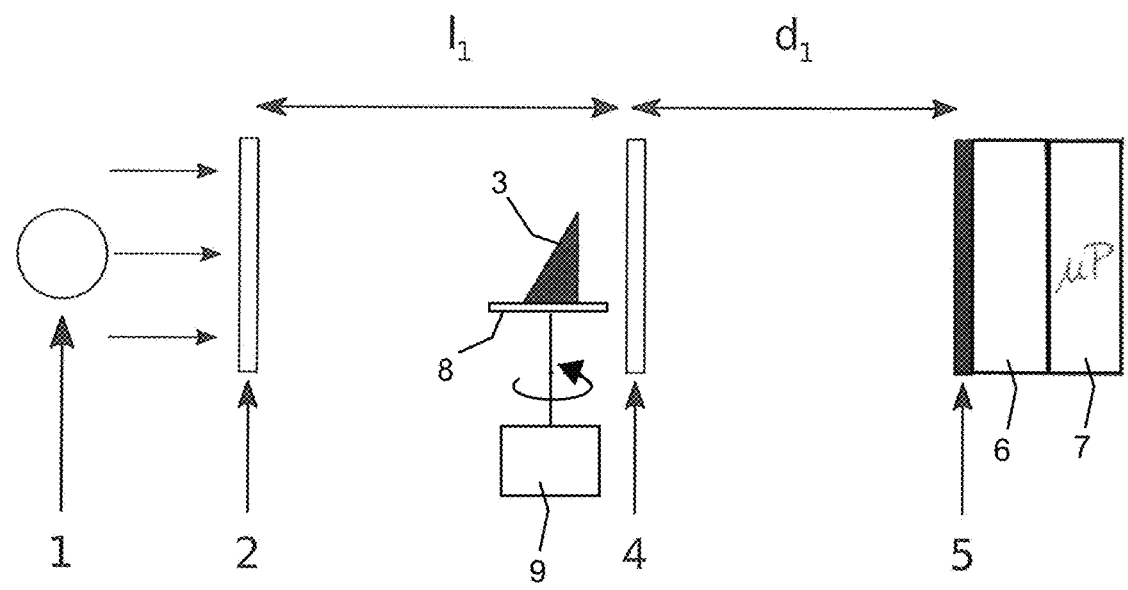
FIG. 1 schematically an experimental setup of a single shot X-ray imaging arrangement.
Figure 1:
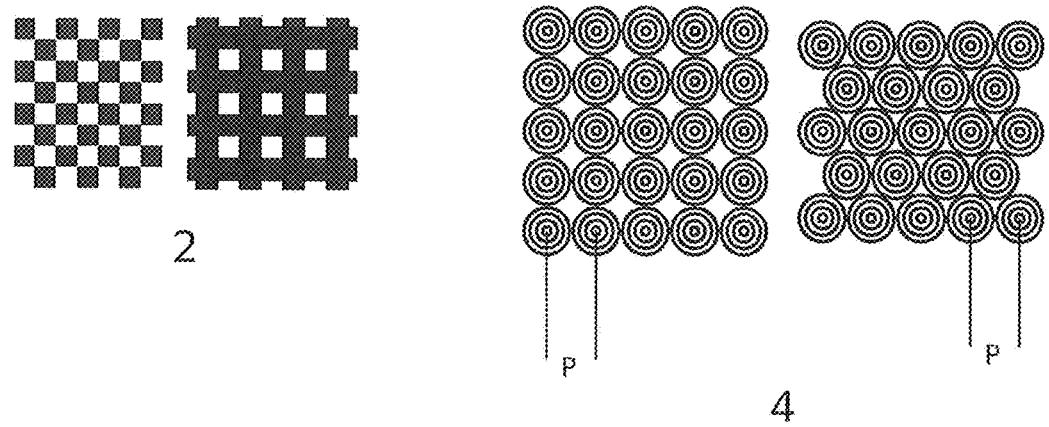

FIG. 1 schematically shows an experimental arrangement for single-shot X-ray imaging. The arrangement comprises an X-ray source 1. In case of a polychromatic X-ray source a source grating 2 can be used. The source grating 2 can have a checkerboard of a grid design as seen in the figure. A sample 3 is placed downstream the source grating 2. Right after the sample 3 a phase shifting or phase-modulating grating 4 is placed. The phase-shifting grating 4 can have the two shown designs; mosaic and honeycomb. An x-ray detector 5 is placed at Talbot distance from the phase-shifting grating 4. A recorder 6 records the images of the detector 5 and a processors 7 evaluates the intensities in a single shot image in order to obtain the characteristics of the sample. A sample handling mechanism 8 can be comprised to place the sample 3 to be investigated between the X-ray source 1 and the phase-modulating structure 4. Preferably, the mechanism to handle the sample 8 may also comprise means for rotating the sample 9.

The single-shot imaging arrangement is capable of omnidirectional scattering sensitivity, acquisition of differential phase contrast signals in vertical and horizontal directions and absorption contrast without the rotation or shift of optical elements or the sample under examination. There are two key components that enable the omnidirectional scattering sensitivity:

1) a dedicated and optimized phase grating design; and
2) a detector with sufficient resolution to resolve the generated interference pattern.

Figure 2:
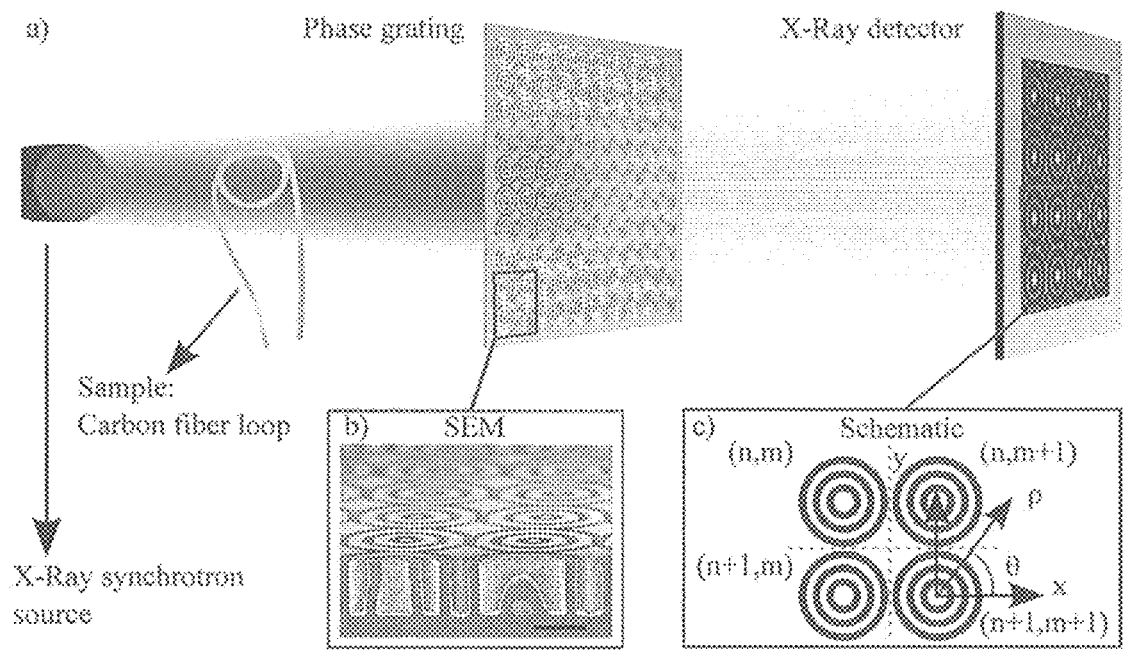
FIG. 2 (a) schematically the experimental setup of FIG. 1 in perspective view; (b) scanning electron microscopy image of fabricated grating (scale bar 10 um), period of unit cell 25 μm and period of each grating 5 μm; (c) schematic of containing all necessary annotation for analyzing the recorded pattern.

These two topics are addressed in FIG. 2 which schematically depicts the experimental setup of FIG. 1 in perspective view (a). FIG. 2(b) shows scanning electron microscopy image of the fabricated phase-shift grating (scale bar 10 μm), having a period of the unit cell of 25 μm and a period of each grating of 5 μm. FIG. 2(c) schematically shows all necessary annotations for analyzing the recorded pattern.

The imaging arrangement according to a preferred embodiment of the present invention comprises the following elements:

An X-Rays source providing radiation for examining the object of interest (probe).

An optional source grating 2 for increasing the coherence of the X-Ray source, the source grating is manufactured from an absorbing material and has a 2D grid or checkerboard design in order to increase coherence of the incoming beam in both horizontal and vertical directions (as shown in FIG. 1).

The phase shifting grating 4 that modulates the phase of the incoming X-Rays by π or π/2. Examples for the dedicated design of the phase grating are depicted in FIG. 2(*a*).

An X-Ray sensitive detector that is adapted to detect radiation after passing through the sample 3 and the phase-shifting grating 4 with a resolution sufficient to record the interference pattern at the distance the detector is placed.

Particularly new in the proposed grating interferometer arrangement is the design of the phase-shifting grating 4. In conventional grating interferometry with linear gratings the scattering signal is detected from the visibility reduction of the interference fringe. Fine structures of the sample cause a local degradation of the coherence of the beam. Coherence is the main regulator of the local fringe visibility. However, linear grating require coherence only in one direction (the normal to the grating lines) in order to produce interference. In contrary, a circular interference pattern would require coherence in all direction (on the imaging plane) in order to generate a self-image with high visibility. A circular covering the whole field of view would only be capable of providing scattering information for different angles through linear segments passing through the center of the grating.

In order to avoid this problem but still exploits the omnidirectional properties of the circular gratings the present invention proposes a design for the phase-shifting grating 4 being composed of a mosaic or a honeycomb repetition of circular gratings as shown in FIGS. 1 and 2(*a*).

In the case of a mosaic repetition the circular gratings (also called unit cell) are repeated with a period of P in horizontal and vertical directions. In the case of the honeycomb arrangement the distance between the centers of neighboring unit cells is again P. The pitch of the circular gratings is p. In order to achieve the maximum filling ratio of the field of view (FOV) p should be a multiple of P, however designs where this condition is not fulfilled are also allowed.

The detector is placed at a Talbot distance defined by the design photon energy of the arrangement and the pitch of the circular gratings p. The interference fringe at the selected Talbot distance can be characterized from the following periodicities: P' and p', where P' the repetition rate of the self-images of the individual circular gratings and p' the period of the self-images of the circular gratings. These periodicities are connected to the design values as following $$p' = \frac{1}{\eta} p \frac{d_1 + l_1}{l_1}, \quad P' = \frac{1}{\eta} P \frac{d1 + l_1}{l_1}$$

where $l_1$ is the distance between the source (or the source grating 2 if the source grating 2 is used) to the phase-shifting grating 4, $d_1$ is the distance between the phase-shifting grating 4 and the generated interference pattern at the detector plane, η=1 for π/2 shift grating while η=2 for it shift grating. The projected period P' defines the pixel size of the reconstructed images of the sample under investigation.

The phase-shifting grating 4 is fabricated in a phase shifting material for the design energy of the imaging arrangement. This means that for low energies the grating can be etched in Si with deep reactive ion etching. For higher energies heavier materials like gold and nickel can be used to reduce the required thickness, at these high energies the required thickness for a phase shift of π or π/2 does not introduce a significant absorption of the incoming X-Rays.

The imaging procedure requires the acquisition of two images. Initially, an image is recorded with only the phase-shifting grating 4 (and the source grating 2 if used) being placed in the x-ray beam. This image will be called the flat image (f). As the next step the sample is introduced into the x-ray beam without shifting or removing the phase-shifting grating 4 and a so-called sample image (s) is recorded.

The analysis procedure starts by locating the self-images of the individual circular gratings on the pixel matrix of the flat image. Due to the circular nature of the grating a maximum is observed in the center, and this maximum is used as a finding criterion for the centers. Once all the centers have been detected a square area of P'×P' around each center is selected and will be noted with the spatial coordinate (n, m) as shown in FIG. 2 *c*). The fringe of each circular grating is approximated by $$I(n, m, \rho, \theta) = A(n, m) + B(n, m, \theta)\cos\left(2\pi \frac{\rho}{\rho'}\right),$$

where A(n, m) denotes the average intensity in the defined area, B(n, m, θ) the angular depend scattering coefficient and ρ, θ are the local coordinates at the unit cell (n, m). The transmission image is calculated as the ratio (sample over flat) of the average values of the recorded interference patterns:

$$T(n, m) = \frac{\Sigma_\theta \Sigma_\rho I_s(n, m, \rho, \theta)}{\Sigma_\theta \Sigma_\rho I_f(n, m, \rho, \theta)}$$

The differential phase contrast images in horizontal and vertical directions are calculated by estimating the shift of the individual circular grating self-images. This can be done by a number of methods, for instance, spatial correlation estimation. Here, a method is proposed based on a linear square fit of the local estimated phase difference between the sample and flat fringes with a theoretical model that is valid for a sinusoidal approximation of the fringes. If the sample fringe is shifted by (x0, y0) then the local phase difference for one circular grating is given by $$\Phi(\rho, \theta, x_0, y_0) = \frac{2\pi}{p'}\left[\sqrt{\rho^2 - x_0^2 - y_0^2 - 2\rho(x_0\cos\theta + y_0\sin\theta)} - \rho\right]$$

The experimental local phase shift is calculated by a Hilbert phase retrieval in the x or y direction. The theoretical model is then fitted to the experimental phase and the values x0 and y0 are estimated.

The directional scattering images are obtained by radial Fourier analysis of the recorded circular fringes. The scattering contrast is calculated by the appropriate Fourier coefficient of the radius of the fringe. The ratio of the Fourier coefficients results in the scatter contrast under that specific angle. Specifically directional scattering images are given by $$C(n, m, \theta) = \frac{R_k^s R_0^f}{R_k^f R_0^f}$$

where $R_k$ is the k-th harmonic of the discrete Fourier transform of the recorded fringe in direction θ and k=P'/p'.

The method was experimentally validated at the TOM-CAT beam line of the Swiss Light Source at Paul Scherrer Institut, CH-5232 Villigen PSI. A phase shifting grating with a radial period of 5 μm and unit cell period of 25 μm was fabricated by e-beam lithography and deep reactive ion etching (DRIE) of Si in house. The grating was etched to a depth of 11 μm which, at 17 keV illumination, produces a phase shift of pi/2. A scanning electron microscopy (SEM) image of the grating can be seen in FIG. 1 (b). The experimental setup is summarized in FIG. 1 (a). The photon energy was selected by a Si 111 monochromator. A pco. edge 4.2 CCD camera with 10 fold magnification (effective pixel size of 0.65 μm) was placed 17 cm behind the phase-shifting grating 4 which corresponds to the first fractional Talbot order.

Figure 3:
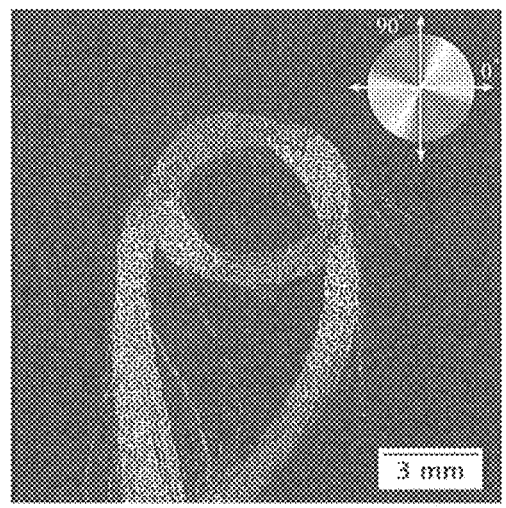
FIG. 3 a directional scattering image of a carbon fiber loop as sample as shown in FIG. 2; the color of the loop represents the most prominent scattering direction.
Figure 4:
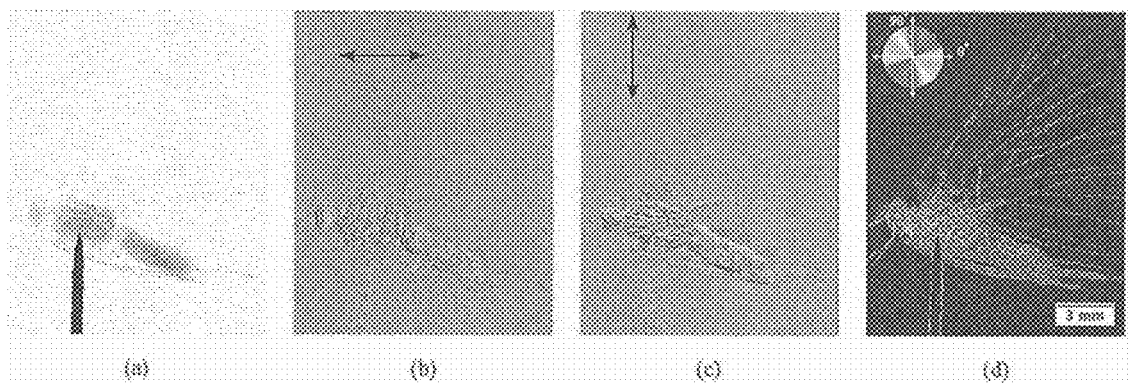
FIG. 4 experimental result of imaging a butterfly; (a) transmission contrast, differential phase contrast in (b) horizontal and (c) vertical direction and (d) directional scattering image.

The directional scattering image of the carbon fiber loop can be seen in FIG. 3. A second sample that was scanned with the same parameters was a butterfly placed on the tip of a steel needle. The resulting transmission, differential phase in horizontal and vertical direction and directional scattering image can be seen in FIG. 4 (a), (b), (c) and (d) respectively.

At the moment appropriate optics are used in order to achieve the necessary resolution to resolve the fringe, however current developments in detector research have made possible resolution enhancement beyond the pixel size of charge integrating hybrid detectors with single photon sensitivity. These developments will allow the application of the method for clinical and industrial applications.

REFERENCE

[1] WO 2011/011014 A1 (US HEALTH [US]; WEN HAN [US]) 27 Jan. 2011 (2011 Jan. 27).

The invention claimed is:

1. A configuration for obtaining quantitative x-ray images from a sample, the configuration comprising:
    an X-ray source outputting x-rays;
    a position-sensitive detector with spatially modulated detection sensitivity having a number of individual pixels;
    a recorder for recording the x-ray images of said position-sensitive detector;
    a processor for evaluating intensities in a single shot image for obtaining characteristics of the sample including absorption, differential phase contrast and directional, small-angle scattering contrast, for specified regions of the pixels;
    a phase-shift periodic structure being:
        i) a 2D periodic structure composed of unit cells, said unit cells being circular gratings, a period of said unit cells is P and that of said circular gratings is p, wherein periodic structures in a circular grating generate a considerable X-ray phase shift difference, which is of π/2 or odd multiples thereof, hereinafter referred to as π/2 shift; or π or π+N×2π, hereinafter referred to as π shift, where N is an integer number; or
        ii) a honeycomb structure composed of unit cells, each unit cell is a circular grating which allows a maximum filling factor of such a periodic structure, periodic structures in said circular grating generate a considerable X-ray phase shift difference, which is of π/2 or odd multiples thereof, hereinafter referred to as π/2 shift; or π or π+N×2π, hereinafter referred to as π shift, where N is an integer number;
said phase-shift periodic structure creates a periodic interference pattern with a repetition of each said unit cell being P' and a period within each said unit cell is p' at a known distance, Talbot effect, downstream on said position-sensitive detector; where P' and p' match a radius of curvature of an incident wavefront by relation $$p' = \frac{1}{\eta} p \frac{d_1 + l_1}{l_1}, P' = \frac{1}{\eta} P \frac{d_1 + l_1}{l_1}$$

where:
    $l_1$ is a distance between said X-ray source and said phase-shift periodic structure; and
    $d_1$ is a distance between said phase-shift periodic structure and a created self-image η=1 for π/2 shift grating while η=2 for π shift grating.

2. The configuration according to claim 1, wherein said phase-shift periodic structure is made by:
    deep etching into silicon, a polymer or similar material, for low energy X-ray photons; or
    depositing a heavy metal into gaps of a low-absorbing structure or grow the heavy metal on a low-absorbing substrate, in either case the heavy metal is used as a phase shift material for high energy X-ray photons.

3. The configuration according to claim 1, further comprising an absorption grating disposed in front of, or embedded into said X-ray source:
    wherein said $l_1$ is a distance between said absorption grating and said phase-shift periodic structure; and
    wherein said absorption grating is a 2D chessboard/mesh-type grating with a pitch of $$p_0 = p \times \frac{l_1}{d_1}$$

or integer multiples thereof.

4. The configuration according to claim 1, further comprising a mechanism being comprised to place the sample to be investigated between said X-ray source and said phase-shift periodic structure, or between said phase-shift periodic structure and said position-sensitive detector.

5. The configuration according to claim 1, wherein an analysis procedure is implemented for obtaining the absorption, the differential phase contrast and directional scattering contrasts of the sample that comprises the steps of recording two intensity images of an interference pattern, one sample image with the sample and one flat image without the sample on said position-sensitive detector.

6. The configuration according to claim 1, wherein said processor detects a location of individual ones of said unit cells on a recorded flat image by using a circular nature of said phase-shift periodic structure, that being said, an intensity maximum is observed in a center of said unit cell.

7. The configuration according to claim 6, wherein said processor calculates a shift between the recorded flat image and a sample image of each said unit cell.

8. The configuration according to claim 1, wherein said processor evaluates a radial visibility reduction for every angle in order to obtain omnidirectional scattering images.

9. The configuration according to claim 1, further comprising means for rotating the sample relatively to remaining components of the configuration to perform data collection for a tomographic scan.

10. The configuration according to claim 1, wherein said phase-shift periodic structure is an absorption grating.

11. The configuration according to claim 1, wherein
the x-rays are hard x-rays; and
said X-ray source is a standard polychromatic X-ray source.

12. The configuration according to claim 6, wherein said processor calculates a shift between the recorded flat image and a sample image of each said unit cell, achieved either with Fourier based methods and/or Hilbert transform methods by calculating an analytical signal or spatial correlation methods.

13. The configuration according to claim 1, wherein said processor evaluates a radial visibility reduction for every angle in order to obtain omnidirectional scattering images accomplished by Fourier methods from the following formula $$(n, m, O) = \frac{R_k^s R_0^f}{R_k^f R_0^f}.$$

14. The configuration according to claim 1, wherein said X-ray source has a 2D array of individual sources that may be mutually incoherent and whose lateral separation is $$p_0 = p \times \frac{l_1}{d_1}$$

or integer multiples thereof.

15. The configuration according to claim 3, further comprising a mechanism being comprised to place the sample to be investigated between said absorption grating and said phase-shift periodic structure, or between said phase-shift periodic structure and said position-sensitive detector.

* * * * *